United States Patent
Zino et al.

(10) Patent No.: US 9,754,372 B2
(45) Date of Patent: Sep. 5, 2017

(54) MARKING OF FLUOROSCOPE FIELD-OF-VIEW

(71) Applicant: BIOSENSE WEBSTER (ISRAEL) LTD., Yokneam (IL)

(72) Inventors: Eliahu Zino, Atlit (IL); Pesach Susel, Haifa (IL); Gil Zigelman, Haifa (IL); Eran Haskel, Kiryat Bialik (IL); Liav Moshe Adi, Haifa (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 321 days.

(21) Appl. No.: 14/460,445

(22) Filed: Aug. 15, 2014

(65) Prior Publication Data

US 2016/0048960 A1 Feb. 18, 2016

(51) Int. Cl.
| | |
|---|---|
| G06K 9/00 | (2006.01) |
| G06T 7/00 | (2017.01) |
| A61B 5/06 | (2006.01) |
| G06T 15/08 | (2011.01) |
| G06T 7/30 | (2017.01) |
| A61B 6/00 | (2006.01) |
| A61B 90/00 | (2016.01) |

(52) U.S. Cl.
CPC ............ *G06T 7/0024* (2013.01); *A61B 5/061* (2013.01); *A61B 6/469* (2013.01); *A61B 6/487* (2013.01); *A61B 6/5217* (2013.01); *A61B 6/5247* (2013.01); *G06T 7/30* (2017.01); *G06T 15/08* (2013.01); *A61B 6/4441* (2013.01); *A61B 6/466* (2013.01); *A61B 6/503* (2013.01); *A61B 2090/376* (2016.02); *G06T 2207/10121* (2013.01)

(58) Field of Classification Search
None
See application file for complete search history.

(56) References Cited

U.S. PATENT DOCUMENTS

| | | |
|---|---|---|
| 5,255,680 A | 10/1993 | Darrow et al. |
| 5,391,199 A | 2/1995 | Ben-Haim |
| 6,239,724 B1 | 5/2001 | Doron et al. |
| 6,332,089 B1 | 12/2001 | Acker et al. |
| 6,484,118 B1 | 11/2002 | Govari |
| 6,618,612 B1 | 9/2003 | Acker et al. |
| 6,690,963 B2 | 2/2004 | Ben-Haim et al. |
| 7,327,872 B2 | 2/2008 | Vaillant et al. |

(Continued)

FOREIGN PATENT DOCUMENTS

| | | |
|---|---|---|
| EP | 1929956 A2 | 6/2008 |
| EP | 2823763 A1 | 1/2015 |
| WO | WO 96/05768 A1 | 2/1996 |

OTHER PUBLICATIONS

EP15181132.0: Extended Search Report: dated Dec. 23, 2015.

*Primary Examiner* — Weiwen Yang
(74) *Attorney, Agent, or Firm* — Louis J. Capezzuto

(57) ABSTRACT

A method includes registering a first coordinate system of a fluoroscopic imaging system and a second coordinate system of a magnetic position tracking system. A three-dimensional (3D) map of an organ of a patient, which is produced by the magnetic position tracking system, is displayed. A 3D volume that would be irradiated by the fluoroscopic imaging system is calculated using the registered first and second coordinate systems. The calculated 3D volume is marked on the 3D map.

8 Claims, 3 Drawing Sheets

(56) References Cited

U.S. PATENT DOCUMENTS

| | | |
|---|---|---|
| 7,706,860 B2 | 4/2010 | McGee |
| 8,303,505 B2 | 11/2012 | Webler et al. |
| 8,515,527 B2 | 8/2013 | Vaillant et al. |
| 8,571,635 B2 | 10/2013 | McGee |
| 2002/0065455 A1 | 5/2002 | Ben-Haim et al. |
| 2003/0120150 A1 | 6/2003 | Govari |
| 2003/0231789 A1 | 12/2003 | Parker et al. |
| 2006/0153468 A1 | 7/2006 | Solf et al. |
| 2008/0137927 A1* | 6/2008 | Altmann ............ A61B 8/4488 382/131 |
| 2008/0183071 A1* | 7/2008 | Strommer ............ A61B 5/06 600/424 |
| 2009/0105579 A1* | 4/2009 | Garibaldi ........ A61B 1/00158 600/409 |
| 2013/0272592 A1 | 10/2013 | Eichler et al. |
| 2014/0050375 A1* | 2/2014 | Baker ............ G06F 19/3481 382/128 |
| 2014/0275998 A1* | 9/2014 | Eichler ............ A61B 6/102 600/424 |

\* cited by examiner

MARKING OF FLUOROSCOPE FIELD-OF-VIEW

FIELD OF THE INVENTION

The present invention relates generally to medical imaging, and particularly to methods and systems for visualization of fluoroscopic system Field-Of-View (FOV) during medical procedures.

BACKGROUND OF THE INVENTION

Minimally invasive medical procedures commonly involve real-time (RT) imaging such as fluoroscopic imaging, sometimes in conjunction with other Three Dimensional (3D) imaging modalities. Several publications deal with registration of RT images with 3D models and 3D maps of patient organs obtained by other modalities.

For example, U.S. Pat. No. 8,515,527, whose disclosure is incorporated herein by reference, describes a method and an apparatus for registering 3D models of anatomical regions of a heart and a tracking system with projection images of an interventional fluoroscopic system.

U.S. Pat. No. 7,327,872, whose disclosure is incorporated herein by reference, describes a method and a system for registering 3D models with projection images of anatomical regions. A first image acquisition system of a first modality employing a catheter at an anatomical region of a patient is configured to produce a first image of the anatomical region using fluoroscopy, the first image comprising a set of fluoroscopy projection images. A second image acquisition system of a second different modality is configured to generate a 3D model of the anatomical region. An anatomical reference system is common to both the first and second image acquisition systems. A processing circuit is configured to process executable instructions for registering the 3D model with the fluoroscopy image in response to the common reference system and discernible parameters associated with the catheter in both the first and second image acquisition systems.

SUMMARY OF THE INVENTION

An embodiment of the present invention that is described herein provides a method including registering a first coordinate system of a fluoroscopic imaging system and a second coordinate system of a magnetic position tracking system. A three-dimensional (3D) map of an organ of a patient, which is produced by the magnetic position tracking system, is displayed. A 3D volume that would be irradiated by the fluoroscopic imaging system is calculated using the registered first and second coordinate systems, and the calculated 3D volume is marked on the 3D map.

In some embodiments, marking the 3D volume includes marking objects of the 3D map that fall inside the 3D volume. In other embodiments, calculating and marking the 3D volume are performed while the fluoroscopic imaging system does not irradiate the patient. In yet other embodiments, the method includes, in response to a change in a position of the fluoroscopic imaging system relative to the organ, recalculating the 3D volume, and re-marking the recalculated 3D volume on the 3D map.

There is additionally provided, in accordance with an embodiment of the present invention, a system including an interface and a processor. The interface is configured to communicate with a fluoroscopic imaging system. The processor is configured to register a first coordinate system of the fluoroscopic imaging system and a second coordinate system of a magnetic position tracking system, to display a three-dimensional (3D) map of an organ of a patient, which is produced by the magnetic position tracking system, to calculate, using the registered first and second coordinate systems, a 3D volume that would be irradiated by the fluoroscopic imaging system, and to mark the calculated 3D volume on the 3D map.

The present invention will be more fully understood from the following detailed description of the embodiments thereof, taken together with the drawings in which:

DETAILED DESCRIPTION OF EMBODIMENTS

Overview

Catheterization processes are used in a variety of therapeutic and diagnostic procedures. Catheter guidance requires imaging capabilities, such as magnetic position tracking. For example, Biosense-Webster, Inc. (Diamond Bar, Calif.) provides the CARTO™ system, used for navigating a catheter in a patient heart.

In some scenarios, it is desirable to operate a fluoroscopic system in parallel with the magnetic position tracking system, in order to acquire a real-time image of the organ in question. Fluoroscopic imaging, however, exposes the patient and staff to potentially-hazardous doses of X-ray radiation. In practice, the Field-Of-View (FOV) of the fluoroscopic system is often narrow, and a considerable portion of X-ray radiation is applied when attempting to position the fluoroscopic system to image the desired area of the organ.

Embodiments of the present invention that are described herein provide improved methods and systems for operating a fluoroscopic system and a magnetic position tracking system. In some embodiments, a processor of the magnetic position tracking system registers the coordinate systems of the fluoroscopic system and the magnetic position tracking system. Using the registration, the processor calculates a volume (e.g., 3D funnel) that would be irradiated by the fluoroscopic system, and marks this volume on a 3D map of the organ produced by the magnetic position tracking system.

The disclosed techniques mark the position of the fluoroscopic system 3D FOV to the physician, without having to activate the fluoroscopic system. Using this technique, the lengthy process of adjusting the fluoroscopic system FOV can be performed without exposing the patient and staff to X-ray radiation. The fluoroscopic system is typically activated only after its FOV is positioned correctly.

Several example visualization techniques are described herein. In some embodiments the processor is configured to mark objects (e.g., anatomical features and medical equipment) falling within the volume of the fluoroscopic system FOV.

System Description

Figure 1:
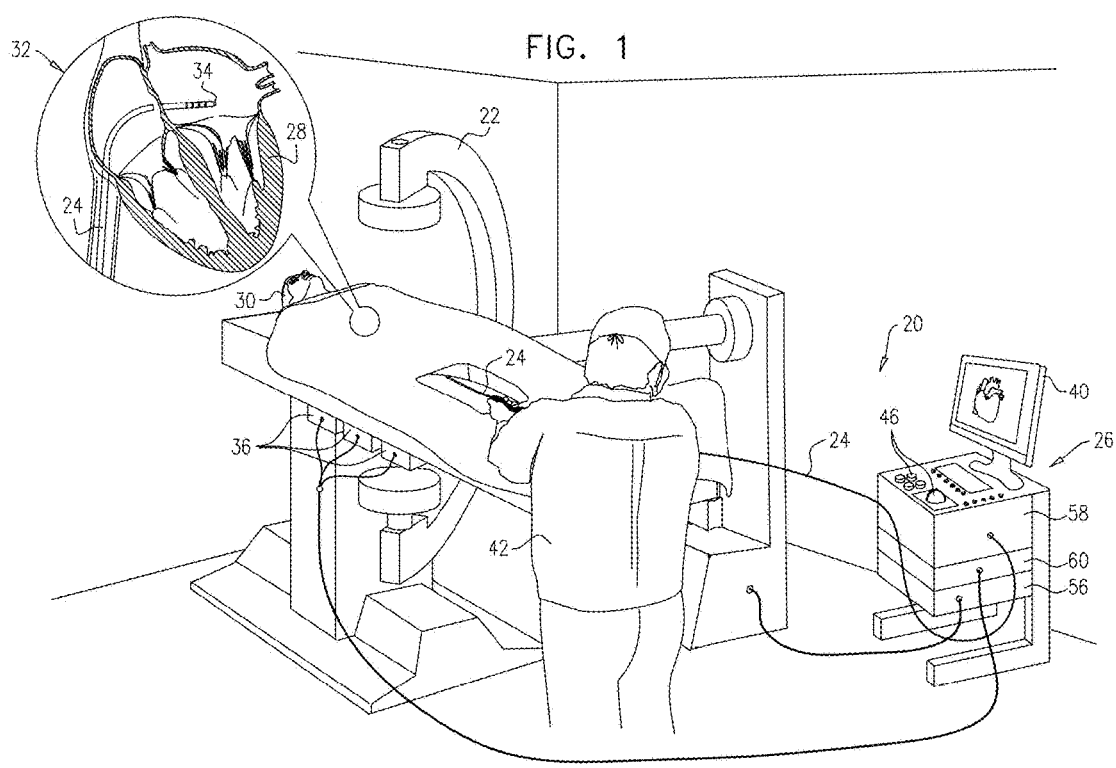
FIG. 1 is a schematic pictorial illustration of a fluoroscopic imaging system and a magnetic position tracking system, in accordance with an embodiment of the present invention.

FIG. 1 is a schematic pictorial illustration of a fluoroscopic imaging system 22 and a magnetic position tracking system 20 during a minimally invasive cardiac procedure, in accordance with an embodiment of the present invention. Fluoroscopic imaging system 22 is connected to magnetic position tracking system 20 via an interface 56. Magnetic position tracking system 20 comprises a console 26, and a catheter 24, which has a distal end 34 as shown in an insert 32 of FIG. 1.

A cardiologist 42 (or any other user) navigates catheter 24 in a patient's heart 28, until distal end 34 reaches the desired location in this organ, and then cardiologist 42 performs medical procedure using catheter 24. In other embodiments, the disclosed techniques can be used with procedures that are performed in any other organ, and instead of cardiologist 42, any suitable user (such as a pertinent physician, or an authorized technician) can operate the system.

This method of position tracking is implemented, for example, in the CARTO™ system, produced by Biosense Webster Inc. (Diamond Bar, Calif.) and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference.

Console 26 comprises a processor 58, a driver circuit 60, interface 56 to fluoroscopic imaging system 22, input devices 46, and a display 40. Driver circuit 60 drives magnetic field generators 36, which are placed at known positions below a patient's 30 torso. In case a fluoroscopic image is needed, cardiologist 42 uses input devices 46 and a suitable Graphical User Interface (GUI) on display 40 to request a fluoroscopic image in patient's heart 28.

Typically, processor 58 calculates and displays a 3D volume (e.g., a funnel-shaped volume) that would be irradiated by fluoroscopic imaging system 22. In other words, the calculated volume marks the FOV of the fluoroscopic system. The calculated 3D volume may have any suitable shape. The description that follows refers mainly to a funnel-shaped volume, for the sake of clarity, and the terms "3D volume" and "3D funnel" are used interchangeably. The calculation can be performed entirely without irradiating X-rays by fluoroscopic imaging system 22.

In some embodiments, processor 58 calculates and displays the 3D volume based on a-priori registration between the coordinate systems of systems 20 and 22. Any suitable registration process can be used for this purpose. In one example process, one or more magnetic position sensors are fitted on moving parts of fluoroscopic system 22. Position tracking system 20 measures the positions of these sensors in the coordinate system of system 20, and is thus able to register the two coordinate systems. In another example process, processor 58 identifies and correlates objects in the 3D magnetic position map (produced by system 20) and in the fluoroscopic images (produced by system 22), and uses the correlation to register the coordinate systems of systems 20 and 22. Additional example registration processes are described in the references cited in the Background section of this application.

In some embodiments, processor 58 creates an overlaid image of the 3D magnetic position tracking map with the calculated fluoroscopic 3D funnel and displays this image on display 40. The overlaid image comprises a marking of the objects of the 3D position tracking map, which fall within the calculated 3D funnel.

The configuration of system 20 shown in FIG. 1 is an example configuration, which is chosen purely for the sake of conceptual clarity. In alternative embodiments, any other suitable configuration can be used for implementing the system. Certain elements of system 20 can be implemented using hardware, such as using one or more Application-Specific Integrated Circuits (ASICs) or Field-Programmable Gate Arrays (FPGAs) or other device types. Additionally or alternatively, certain elements of system 20 can be implemented using software, or using a combination of hardware and software elements.

Processor 58 typically comprises a general-purpose computer, which is programmed in software to carry out the functions described herein. The software may be downloaded to the computer in an electronic form, over a network, for example, or it may, alternatively or additionally, be provided and/or stored on non-transitory tangible media, such as magnetic, optical, or electronic memory.

Overlay of Simulated 3D Fluoroscopic Funnel on 3D Map

In some embodiments, processor 58 of system 20 displays a 3D map of patient's heart 28 comprising distal end 34, so cardiologist 42 knows the exact location of distal end 34 with respect to the pertinent area in heart 28. During the navigation and treatment process, cardiologist 42 may need images of the pertinent organ around or near distal end 42. The embodiments described herein fulfill the need for minimizing X-ray irradiation while acquiring a 3D fluoroscopic image.

In a typical flow, in case a fluoroscopic image is needed in the vicinity of the catheter's distal end, cardiologist 42 defines the desired area by positioning fluoroscopic imaging system 22 to point to the desired location. Processor 58 of system 20 calculates a simulated volume (e.g., 3D funnel) that would be irradiated by fluoroscopic imaging system 22 on the area in patient's heart 28 where fluoroscopic imaging system is pointing, without irradiating X-rays by fluoroscopic imaging system 22.

Processor 58 creates an overlaid image of the 3D magnetic position tracking map with the calculated 3D funnel and displays this image on display 40. In some embodiments, the overlaid image comprises markers of the elements which appear in the calculated 3D funnel and in the pertinent frame of the 3D magnetic position tracking map. The marked elements may comprise, for example, objects of patient's heart 28 or other organ falling inside the simulated fluoroscopic 3D funnel, and catheter's distal-end 34, if it falls into the same 3D funnel.

In various embodiments, processor 58 may mark the calculated 3D volume in various ways. For example, processor 58 may distinguish the 3D volume, and/or objects in the volume, using different colors, different intensities, different contrasts, or using any suitable visualization means.

Cardiologist 42 examines the presented markers on display 40. If the markers comprise the desired objects in patient's heart 28, and distal-end 34, then fluoroscopic imaging system 22 is positioned accurately and ready to acquire a 3D fluoroscopic image. If the markers do not comprise the desired objects in patient's heart 28 or distal-end 34, fluoroscopic imaging system 22 is not positioned at the desired location.

Typically, when cardiologist 42 concludes that fluoroscopic imaging system 22 is positioned in the desired location, he uses operating console 26 to request from fluoroscopic imaging system 22 to acquire a fluoroscopic image by irradiating the patient with ionizing X-rays. In case of a positioning mismatch, cardiologist 42 moves patient 30 with respect to the irradiation head of fluoroscopic imaging system 22, until the 3D funnel reaches the desired location. Only then, cardiologist 42 (or another user) uses console 26 to request fluoroscopic imaging system 22 to acquire a fluoroscopic image and to collect the relevant information required to continue the medical procedure.

In some embodiments cardiologist 42 may decide whether the 3D funnel is located at the right position by looking at the overlaid image with markers in screen 40. In alternative embodiments, processor 58 may decide autonomously whether the 3D funnel is located in the desired location (e.g., if distal-end 34 is in the center of the 3D funnel's FOV) and recommend the medical staff to acquire a fluoroscopic image.

Depending on the Fluoroscopic system orientation, the catheter can be centered in the funnel's FOV at various angles, whereas the cardiologist may be interested in a specific viewing angle. In some embodiments, cardiologist 42 specifies the required angle and imaging criteria. In response, processor 58 calculates the new position, illumination angle, and relative orientation required in system 22, and instruct the system or the operator how to operate system 22 to accomplish the new state.

Figure 2:
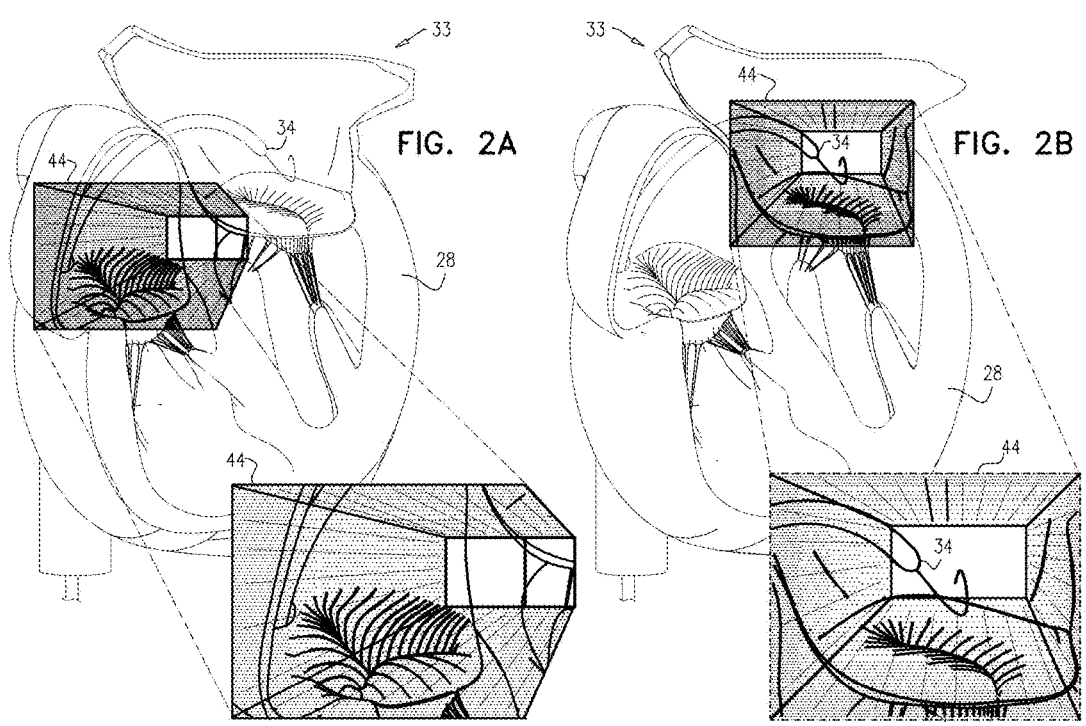
FIGS. 2A and 2B are schematic pictorial illustrations of a simulated fluoroscopic system FOV overlaid on a 3D magnetic position tracking map, in accordance with an embodiment of the present invention.

FIG. 2A is a schematic pictorial illustration of a simulated fluoroscopic 3D funnel 44, overlaid on a 3D magnetic position tracking map 33, in accordance with an embodiment of the present invention. An image of this sort is displayed by processor 58 on display 40. Processor 58 calculates the location of simulated fluoroscopic 3D funnel 44 on 3D magnetic position tracking map 33, based on the aligned coordinates of fluoroscopic imaging system 22 and magnetic position tracking system 20. Processor 58 presents the overlaid image, with marked elements in the 3D funnel's Field of View (FOV), on display 40.

In the example that is presented in FIG. 2A, simulated 3D funnel 44 FOV is not positioned in the target location. Distal-end 34 should be located at the center of the FOV of simulated 3D funnel 44, and in this example, distal-end 34 is not even within this FOV. In the example of FIG. 2A, cardiologist 42 examines 3D funnel 44 overlaid on 3D map 33 of FIG. 2A and concludes that he/she should request to move the 3D funnel's FOV up-and-right so distal-end 34 is located in the center of the 3D funnel's FOV.

FIG. 2B is a schematic pictorial illustration of simulated fluoroscopic 3D funnel 44, overlaid on 3D magnetic position tracking map 33, in accordance with an embodiment of the present invention. In this example, cardiologist 42 has moved the FOV of 3D funnel 44 up-and-right from its location in FIG. 2A, and positioned the simulated fluoroscopic 3D funnel's 44 FOV in the desired location where distal-end 34 is in the center of the simulated fluoroscopic 3D funnel's FOV, as shown in FIG. 2B.

In an embodiment, FIG. 2B is obtained by processor 58, which calculates the location of simulated fluoroscopic 3D funnel's 44 FOV and presents it on screen 40, overlaid on 3D magnetic position tracking map 33, with markers of pertinent elements falling within this FOV.

As shown in FIG. 2B, distal-end 34 is located in the center of simulated fluoroscopic 3D funnel's 44 FOV and pertinent objects are marked accordingly. In some embodiments this accurate positioning of fluoroscopic imaging system 22 with respect to patient 30 and magnetic position tracking system 20, is obtained based on the presented technique, without exposing patient 30, cardiologist 42, and other individuals in the operating room, to excess X-ray radiation.

Based on the image shown in FIG. 2B, which is created by processor 58 and presented on display 40, cardiologist 42, or any other suitable user, may proceed to use fluoroscopic imaging system 22 and to acquire a fluoroscopic image the desired location in patient's heart 28, which may comprise distal-end 34 in the same FOV.

Figure 3:
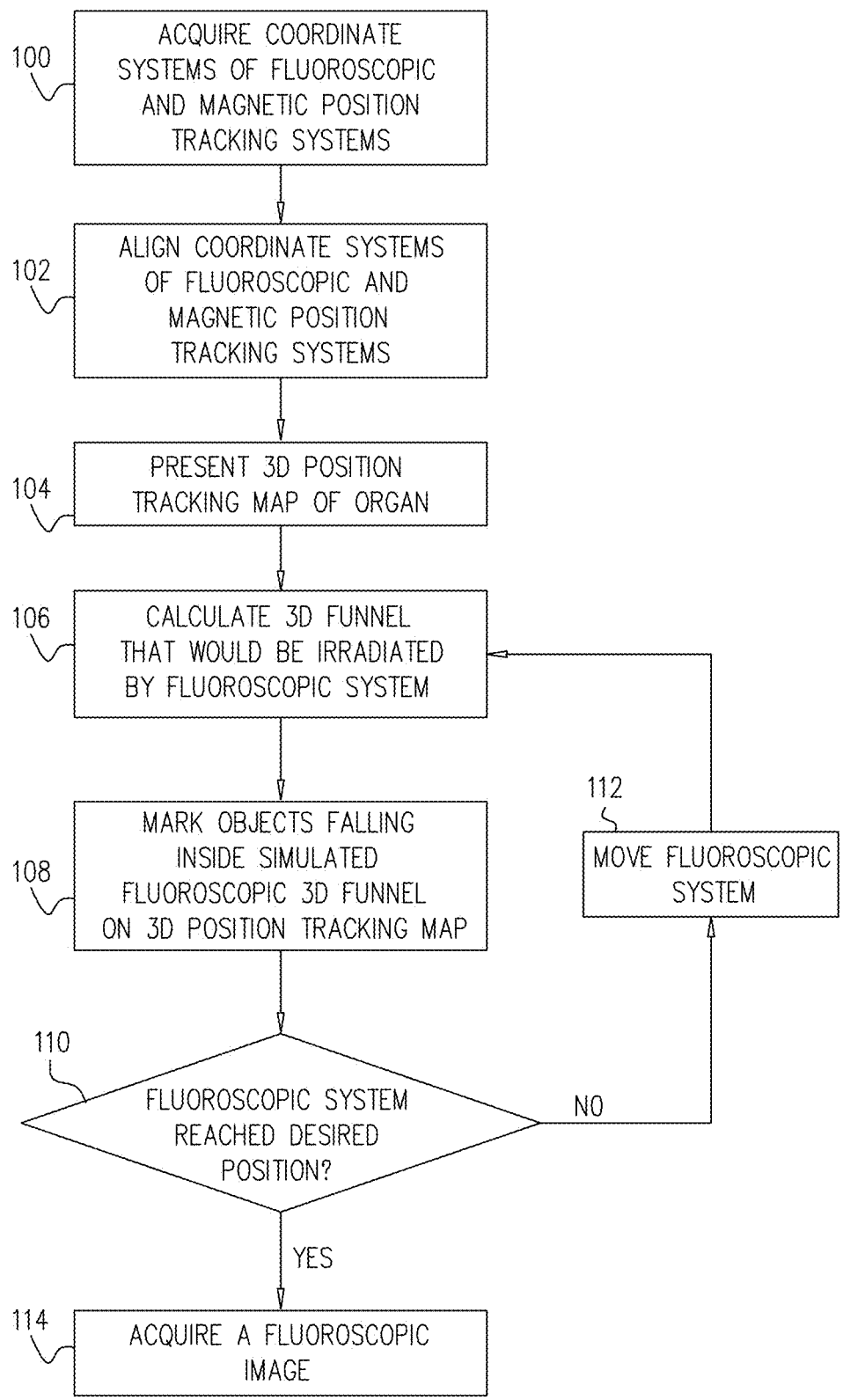
FIG. 3 is a flow chart that schematically illustrates a method for visualizing a simulated fluoroscopic system FOV, in accordance with an embodiment of the present invention.

FIG. 3 is a flow chart that schematically illustrates a method for minimizing irradiation of X-rays using markers of a simulated fluoroscopic 3D funnel 44 on a position tracking map 33, in accordance with an embodiment of the present invention.

The method begins at a coordinate acquisition step 100, where processor 58 acquires the coordinate systems of fluoroscopic imaging system 22 and magnetic position tracking system 20. At a coordinate alignment step 102, processor 58 aligns the coordinate systems of fluoroscopic imaging system 22 and magnetic position tracking system 20, in order to match positions of a pertinent organ in patient 30 at both systems.

At a position tracking presentation step 104, processor 58 presents 3D position tracking map 33 of a given organ of patient 30. In an embodiment, the organ is heart 28, but may be any pertinent organ of patient 30 in other embodiments. At a 3D funnel calculation step 106, processor 58 receives the planned irradiation setup parameters of fluoroscopic imaging system 22 via interface 56, and calculates the 3D funnel that would be irradiated by fluoroscopic imaging system 22 on the pertinent organ of patient 30.

At an object marking step 108, processor 58 applies the calculated 3D funnel obtained at 3D funnel calculation step 106 and the position of fluoroscopic imaging system 22 with respect to magnetic position tracking system 20, to mark objects falling inside simulated fluoroscopic 3D funnel 44, on position tracking map 33. As a result, cardiologist 42 can see on display an overlaid image of position tracking map 33 with marked objects that would be obtained in case cardiologist 42 applies fluoroscopic imaging system 22.

At a decision step 110, cardiologist 42 examines the overlaid image comprising markers of simulated fluoroscopic 3D funnel 44 and decides whether fluoroscopic imaging system 22 is positioned at the desired location to acquire a 3D fluoroscopic image. If cardiologist 42 decides that fluoroscopic imaging system is positioned at the desired location, he/she uses input devices 46 and GUI on display 40 to command fluoroscopic imaging system 22 (via processor 58 and interface 56) to acquire a fluoroscopic image, at an image acquisition step 114. Note that all the method steps prior to step 114 are typically performed while fluoroscopic system 22 does not emit X-ray radiation.

If cardiologist 42 decides that fluoroscopic imaging system 22 is not positioned at the desired location, the cardiologist repositions the fluoroscopic system relative to the patient, at a repositioning step 112. At this point, in various embodiments, the method may loop back to various previous stages of the process.

In one embodiment, the flow loops back to 3D funnel calculation step 106, in which processor 58 recalculates the 3D funnel that would be irradiated by fluoroscopic imaging system 22 on the pertinent organ of patient 30.

In the description above, the process of recalculating and visualizing the position of the fluoroscopic system FOV is continuous and on-going. In alternative embodiments, however, recalculation can be triggered by an event, e.g., in response to detecting motion of the fluoroscopic system or in response to a request from the user.

Although the embodiments described herein mainly address cardiology applications, the methods and systems described herein can also be used in other applications that involve mapping registered with Fluoroscopic imaging.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method, comprising;
    registering a first coordinate system of a fluoroscopic imaging system and a second coordinate system of a magnetic position tracking system;
    displaying a three-dimensional (3D) magnetic position tracking map of an organ of a patient, which is produced by the magnetic position tracking system;
    calculating, based on aligned coordinates of the registered first and second coordinate systems, a 3D volume that would be irradiated by the fluoroscopic imaging system according to a direction in which the fluoroscopic imaging system is pointing; and
    marking the calculated 3D volume on the 3D magnetic position tracking map.

2. The method according to claim 1, wherein marking the 3D volume comprises marking objects of the 3D map that fall inside the 3D volume.

3. The method according to claim 1, wherein calculating and marking the 3D volume are performed while the fluoroscopic imaging system does not irradiate the patient.

4. The method according to claim 1, and comprising, in response to a change in a position of the fluoroscopic imaging system relative to the organ, recalculating the 3D volume, and re-marking the recalculated 3D volume on the 3D map.

5. A system, comprising;
    an interface, which is configured to communicate with a fluoroscopic imaging system; and
    a processor, which is configured to register a first coordinate system of the fluoroscopic imaging system and a second coordinate system of a magnetic position tracking system, to display a three-dimensional (3D) magnetic position tracking map of an organ of a patient, which is produced by the magnetic position tracking system, to calculate, based on aligned coordinates of the registered first and second coordinate systems, a 3D volume that would be irradiated by the fluoroscopic imaging system according to a direction in which the fluoroscopic imaging system is pointing, and to mark the calculated 3D volume on the 3D magnetic position tracking map.

6. The system according to claim 5, wherein the processor is configured to mark objects of the 3D map that fall inside the 3D volume.

7. The system according to claim 5, wherein the processor is configured to calculate and mark the 3D volume while the fluoroscopic imaging system does not irradiate the patient.

8. The system according to claim 5, wherein the processor is configured to recalculate the 3D volume, and re-mark the recalculated 3D volume on the 3D map, in response to a change in a position of the fluoroscopic imaging system relative to the organ.

* * * * *